United States Patent [19]
Witzeman et al.

[11] Patent Number: 5,359,125
[45] Date of Patent: Oct. 25, 1994

[54] THERMOSETTING COATING COMPOSITIONS

[75] Inventors: J. Stewart Witzeman, Kingsport; Allen L. Crain, Blountville, both of Tenn.

[73] Assignee: Eastman Chemical Company, Kingsport, Tenn.

[21] Appl. No.: 103,622

[22] Filed: Aug. 9, 1993

Related U.S. Application Data

[62] Division of Ser. No. 709,049, Jun. 3, 1991, Pat. No. 5,247,122.

[51] Int. Cl.$^5$ ............................................. C07C 69/76
[52] U.S. Cl. ........................................ 560/54; 560/176
[58] Field of Search ................................. 560/176, 54

[56] References Cited

U.S. PATENT DOCUMENTS

| | | | |
|---|---|---|---|
| 2,101,217 | 12/1937 | Hill et al. | 560/176 |
| 2,665,304 | 1/1954 | Patrick | 560/176 |
| 3,201,253 | 8/1965 | Wilson et al. | 96/107 |

FOREIGN PATENT DOCUMENTS

| | | |
|---|---|---|
| 93945 | 11/1983 | European Pat. Off. . |
| 784101 | 7/1935 | France . |
| 1710545 | 2/1992 | U.S.S.R. . |

OTHER PUBLICATIONS

Encyclopedia of Polymer Science & Engineering, vol. 4, pp. 350–395 1956.
Näslund et al, Acta Chemica Scandinavica, 16, (1962) 1329–1336.
Astle et al; Industrial & Engineering Chemistry, v. 44 (1952) 2867.
Chemical Abstracts, vol. 61, 13280g, 1964.
B. D. Wilson, *J. Org. Chem.*, 28, 314 (1963).
Emelina et al., *J. Org. Chem. U.S.S.R.*, 23 (1987) 2263.
I. L. Finar, J. Chem. Soc. (1961) 674.
Journal of the Chemical Society, vol. 1959, No. III, Aug., 1959, Letchworth GB, pp. 2539–2547; Cornforth et al, "A Stereoselective Synthesis of Squalene", p. 2541; Example XXIV.

*Primary Examiner*—Paul J. Killos
*Attorney, Agent, or Firm*—Bernard J. Graves, Jr.

[57] ABSTRACT

Disclosed are certain novel 2,2′-bisacetoacetates useful as crosslinking agents and a process for the preparation therefor. Also provided are novel enamel compositions containing the crosslinkers and coatings and articles coated with thermosetting coating compositions crosslinked with these novel crosslinkers.

4 Claims, No Drawings

THERMOSETTING COATING COMPOSITIONS

This is a divisional application of copending application Ser. No. 07/709,049 filed on Jun. 3, 1991, now U.S. Pat. No. 5,247,122.

FIELD OF THE INVENTION

This invention belongs to the field of organic chemistry. More particularly, it relates to certain 2,2'-bisacetoacetates which are useful as polymer crosslinking agents in thermosetting coating compositions.

BACKGROUND OF THE INVENTION

Polymer crosslinking agents or "crosslinkers" are multi-functional molecules capable of reacting with pendant functional groups on polymers. The use of crosslinkers enable one to increase the molecular weight of the polymer, usually in a second step, and thus improve the properties of the resulting polymer or polymeric film. Most crosslinking reactions are initiated by heating a mixture of the polymer and the crosslinker either neat or in a solvent. Such systems are often referred to as "thermosetting" systems.

Crosslinkers are particularly useful in coating applications due to the fact that the crosslinker enables the use of relatively low molecular weight polymers and resins which are easily handled in solvents. The formulation can subsequently be applied to the substrate and heated, or cured, to give the finished (thermoset) coating. This makes it possible to take advantage of the ease of handling and solubility characteristics of the lower molecular weight resins used in the formulation and subsequently develop the hardness, chemical and solvent resistance, as well as strength/flexibility properties desired in the ultimate coating by the reaction of the crosslinker with the resin during the curing process.

Crosslinkers are becoming increasingly important due to the emphasis on more environmentally acceptable coatings. One major environmental concern in the coatings industry is the amount of organic solvent released during the curing process. This solvent level or Volatile Organic Content (VOC) is of concern due to the role of organic solvents in the development of photochemical smog. For these reasons various governments, including the U.S., are regulating the VOC levels of coating formulations. One way to reduce the amount of solvent necessary in a coating formulation is to reduce the molecular weight of the resin backbone used in the formulation. When this approach is used, how-ever, crosslinking becomes even more critical to the development of the ultimate properties in the cured film. Thus in these applications the crosslinker enables a more environmentally sound coating formulation.

PROPERTIES OF CROSSLINKED FILMS AND COATINGS

A number of properties are desired in a coating in order to impart the desired protection of the object from corrosion and other environmental factors. Some of the protective characteristics that are ultimately desired include the resistance of the coating to various chemicals and solvents, the impact strength of the system, the hardness of the coating and the weather-ability, or resistance of the system to various factors related to environmental exposure.

I) Chemical and Solvent Resistance

In order for a coating to impart adequate protection to the object coated it must be resistant to various chemicals and solvents. If a coating is not resistant to solvents and chemicals, the coating could be removed or the protective integrity compromised by exposure to commonly used materials such as cleaners or gasoline. Since the coating formulation is usually applied in a solvent, development of solvent resistance in the cured film indicates a change in the chemical nature of the coating formulation. This change can be attributed to the crosslinking of the polymer. A commonly used test to assay this property is the methyl ethyl ketone (MEK) rub resistance of the coating. The MEK rub resistance of a coating is often one of the best diagnostic tests for determining the extent of cross-linking in coatings. For most applications, a MEK rub resistance of greater than 175-200 is generally desired.

II) Impact Strength

In order for a coating to be resistant to collisions and other sudden impacts the material must have certain strength characteristics. If a coating does not possess enough strength, impacts and/or collisions will lead to chipping and breaking of the coating which, in turn, compromise the protective integrity of the film. A commonly used test for the impact strength of a coating (ASTM D2794-84) is to drop a weight from various heights on a coated panel and determine the force(in foot-lbs.) required to break the coating. Proper crosslinking can help develop the impact strength of a coating.

III) Hardness

In order for a coating to be resistant to scratching and other such abrasions the coating must possess a certain degree of hardness. This resistance to scratching is often determined by marring the coating with pencils of various hardness and noting which hardness of pencil actually scratches the coating.

Hardness and impact strength often work in opposite directions. This is due to the fact that impact strength reflects both the strength and the flexibility of the polymeric film, while hardness reflects primarily just the strength or rigidity of the film. Thus one often seeks a combination of hardness and flexibility by compensating one of the above characteristics for the other.

The compensation of these two factors is best understood by invoking the theory of crosslink density. If the coating formulation consists of a group of poly-functional (n>2) polymer molecules and crosslinker then the crosslinking process can be thought of as consisting of a series of steps. Initially, the crosslinking reaction consists of intermolecular reactions of various polymer chains. During the initial phase the polymer and crosslinker chains are combining and thus building in molecular weight, but, the mobility of the resulting polymer chains is not greatly restricted. This stage would be characterized by improvement in the chemical resistance, hardness and impact strength of the film. At some point, however, intermolecular reaction.is essentially complete and intramolecular reaction becomes significant. At this point the polymer becomes more rigid due to restriction of the polymer chain mobility by these intramolecular reactions and the resulting coating becomes more brittle. At this stage hardness will improve but the impact strength will decrease, due to the increased rigidity of the polymer network. The balance between flexibility and hardness can be controlled by the amount of crosslinker used, the average functionality of the polymer and crosslinker as well as the chemical structure of the polymer or cross-linker.

IV) Resistance to Atmospheric Exposure (Weathering)

Since many coated objects are exposed to severe weather conditions the performance of the coating under various exposure conditions is very important. Factors which effect the weatherability of the coating include the composition of the polymer and the cross-linker, as well as the degree of crosslinking. A variety of exposure tests are available which enable one to determine the performance of the system to severe conditions.

CROSSLINKERS CURRENTLY USED IN THE FIELD

A large number of crosslinkers are used in various applications. A partial list of the more commonly used functional groups used in crosslinkers include:

Epoxy Compounds
Isocyanates
Amino resins
Unsaturated compounds

These materials take advantage of the reaction of the aforementioned functional groups with various pendant groups on the polymeric backbone. These cross-linkers can be used in combination with other cross-linkers to impart a variety of desired characteristics to the coatings. The use and reactions of these cross-linkers have been reviewed elsewhere. (See, for example, Labana, S.S., in *Encyclopedia of Polymer Science and Engineering*, Vol. 4, pp. 350–395. All of these materials are structurally very different from the 2,2'-bis($C_1$-$C_6$ alkyl acetoacetates) in the present invention as described below.

SUMMARY OF THE INVENTION

The present invention provides various novel 2,2'-bisacetoacetates useful as crosslinking agents in thermosetting coating compositions, and a process for the preparation therefor. Further provided are novel curable enamel compositions comprised of the above novel 2,2'-bisacetoacetate crosslinking agents.

DETAILED DESCRIPTION OF THE INVENTION

The present invention provides compounds of Formula (1):

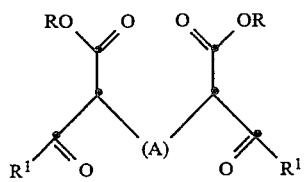

wherein R is $C_4$-$C_{10}$ tertiary alkyl; $R^1$ is $C_1$-$C_6$ alkyl or aryl; and A is a group of the formula

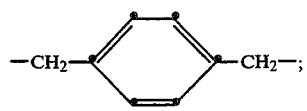

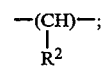

wherein $R^2$ is phenyl; or A is a $C_1$-$C_{10}$ hydrocarbyl radical.

Compounds of Formula (1) above are useful as crosslinking agents in thermosetting coating compositions as described more fully below. Others have reported attempts to prepare 2,2'-bis(alkyl aceto-acetates) (Wilson, B. D.; J. Org. Chem. 28, 314, (1963). Smith, W. T.,Kort, P. G.; *J. Am. Chem. Soc.*, 72, 1877 (1950). Emelina, E. E.; Gindin, V. A.; Ershou, B. A.; J. Org. Chem. USSR (Engl. Trans.) 23, 2263 (1987). Mastagli, P.; Lambert, P., Andric, N.; Bull. Soc. Chim. France 1956, 795. Finor, I. L.; J. Chem. Soc. 1961, 674. NasLund, G.; Senning, A.; Lawesson, S-O; Act. Chem. Scand. 16, 1329 (1962).)

Further, it is well documented that compounds like the above wherein

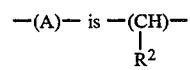

can be difficult to isolate due to the subsequent cyclization to give the cyclohexyl compound of Formula (2)

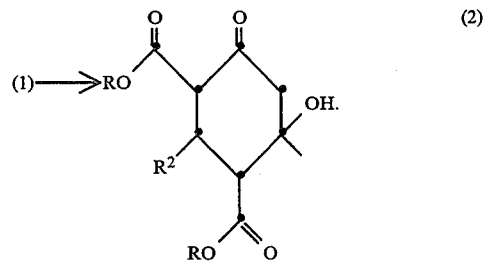

As a further aspect of the present invention there is provided a process for preparing compounds of Formula (I)

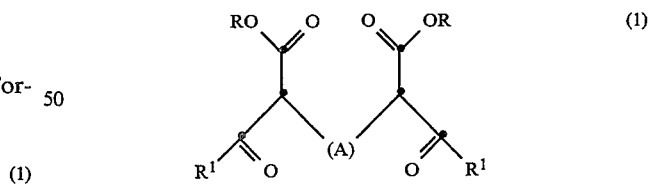

wherein A is —$CH_2$—, and $R^1$ is $C_1$-$C_6$ alkyl or aryl, which comprises contacting a mixture of $C_4$-$C_{10}$ tertiary alkyl beta-keto ester of the formula

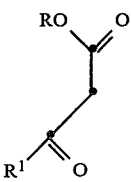

and aqueous formaldehyde with a basic ion exchange resin.

In the above process, it is preferred that the aqueous formaldehyde solution contain about 20 to about 35% of formaldehyde relative to water.

The basic ion exchange resin used in the process can be any strongly basic ion exchange resin. These materials are typically derived from either styrene/divinyl benzene polymers or from acrylic/divinyl benzene polymers and contain a quaternary amine/hydroxide complex. Examples of these resins include Amberlite IRA-400, 402/440, 938, 900 and IRA 458 from Rohm and Haas; Duolite A-109, A-161 and A-132 also from Rohm and Haas; and Dowex SBR-P, SBR and MSA-1 from Dow Chemical.

It is further preferred that the process be carried out at a temperature of about 18° C. to about 40° C., with 25°-35° C. being especially preferred.

As a further aspect of the present invention, there is provided a curable enamel composition comprising
(a) about 95 to about 55 weight percent, based on the total weight of (a) and (b), of one or more curable polymers;
(b) about 5 to about 45 weight percent, based on the total weight of (a) and (b), of a compound of Formula (1)

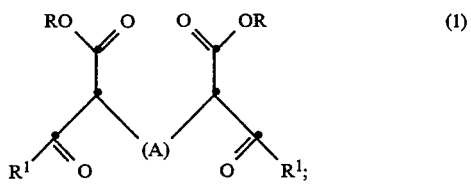

wherein R is $C_4$-$C_{10}$ tertiary alkyl; $R^1$ is $C_1$-$C_6$ alkyl or aryl, and A is a group of the formula

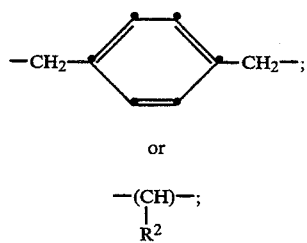

wherein $R^2$ is phenyl; or A is a $C_1$-$C_{10}$ hydrocarbyl radical;
(c) about 0 to about 50 weight percent, based on the total weight of (a) and (b), of a solvent.

As used herein to describe curable enamel compositions, all weight percentages refer to the total weight to (a) and (b), i.e., binder. Thus if the total weight of (a) and (b) in a given composition is 100 g, the total weight of component (c) present would be 0 to 50 g (likewise with respect to component (d) as set forth below).

It is further preferred that component (a) is present in a range of about 85 to 60 weight percent, that component (b) is present in a range of about 15 to 40 weight percent, and that component (c) is present in a range of about 0 to 35 weight percent. Component (a) can be any curable polymer with free hydroxy groups. Examples of such polymers include the polyester and acrylic type polymers.

The curable polyester component (a) can be prepared by condensation polymerization methods known per se in the art. The most preferred method is to melt all reactants in a suitably sized reactor, heat the reactants to initiate the reaction and continue processing until the desired molecular weight is reached. Reaction is evidenced by the collection of water (direct condensation) or alcohol (ester inter-change). This procedure is referred to as fusion processing and can be conducted at atmospheric pressure or under vacuum. No modifications in these standard procedures are required for preparing suitable polymers for component (a), above.

In such curable polyesters, suitable diol andL/or polyol residues are preferably selected from residues of ethylene glycol; propylene glycol; 1,3-propanediol; 2,4-dimethyl-2-ethylhexane-1,3-diol; 2,2-dimethyl-1,3-2-ethYl-2-butyl-1,3-propanediol; 2-ethyl-2-isobutyl-1,3-propanediol; 1,3-butanediol; 1,4-butane-diol; 1,5-pentanediol, 1,6-hexanediol, 2,2,4-trimethyl- 1,3-pentanediol; thiodiethanol; 1,2-cyclohexane-dimethanol; 1,3-cyclohexanedimethanol; 1,4-cyclohexane-dimethanol; 2,2,4,4-tetramethyl-1,3-cyclobutanediol; p-xylylenediol; diethylene glycol, triethylene glycol; tetraethylene glycol; and pentaethylene, hexaethylene, heptaethylene, octaethylene, nonaethylene, and decaethylene glycols.

Further, preferably the carboxylic acid residues of the curable polyesters are selected from residues of oxalic, malonic, dimethylmalonic; succinic; glutaric; adipic; trimethyladipic; pimelic, 2,2-dimethylglutaric; azelaic; sebacic, fumaric; maleic; itaconic; 1,3-cyclopentanedicarboxylic; 1,2-cyclohexanedicarboxylic; 1,3-cyclohexanedicarboxylic; 1,4-cyclohexanedicarboxylic; phthalic; terephthalic; isophthalic; 2,5-norbornanedicarboxylic; 1,4-naphthalic; diphenic; 4,4'-oxydi-benzoic, diglycolic; thiodipropionic; 4,4'-sulfonyl-dibenzoic; and 2,6-naphthalenedicarboxylic acids.

Examples of commerically-available curable polyesters (component (a)) include Cargill 5770, Cargill 5722, and Aroplaz 6455 (Spencer Kellogg). In general, such polyesters will have hydroxyl values of about 20 to 200 (mg KOH/g polymer).

The acrylic polymer component (a) is preferably a polymer or resin prepared by polymerization of a hydroxyl-bearing monomer such as hydroxyethyl methacrylate, hydroxyethyl acrylate, hydroxyhexyl acrylate, hydroxyhexyl methacrylate, hydroxypropyl acrylate, hydroxypropyl methacrylate, hydroxybutyl acrylate, hydroxylbutyl methacrylate and the like optionally polymerized with other monomers such as methyl acrylate, methyl methacrylate, ethyl acrylate, ethyl methacrylate, butyl acrylate, butyl methacrylate, isobutyl acrylate, isobutyl methacrylate, ethylhexyl acrylate, ethylhexyl methacrylate, styrene, vinyl acetate, and the like. The ratio of reagents and molecular weights of the resulting acrylic polymer are preferably chosen so as to give polymers with an average functionality (the number of OH groups per molecule) greater than or equal to 2, preferably greater than or equal to 4.

Examples of commercially-available curable acrylic polymers include Joncryl 800, Joncryl 500, and Neocryl LE-800.

Suitable solvents for the curable enamel composition (component (b)) include ketones, (for example, methyl amyl ketone); glycol ethers such as 2-butoxy-ethanol; glycol ether esters such as ethyl-3-ethoxy-propionate(EEP) and methoxy propyl acetate; toluene; ester solvents such as ethyl acetate, butyl acetate, propyl acetate, and the like; alcohols such as butanol; 1-methyl-2-pyrrolidinone; xylenes; and other volatile inert solvents typically used in industrial baking (i.e., thermosetting) enamels.

The term $C_1$-$C_{10}$ hydrocarbyl radical preferably denotes a divalent alkylene group. Examples of such groups include methylene, ethylene, propylene, and the like.

The term "aryl" as used herein refers to heterocyclic aryl rings and carbocyclic aryl rings. For example, aryl can be phenyl, naphthyl, phenanthryl, and the like. Aryl can also be 5 or 6-membered heterocyclic aryl rings containing one oxygen atom, ancot one sulfur atom, and up to three nitrogen atoms, said heterocyclic aryl ring optionally fused to one or two phenyl rings. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo, pyridazinyl and purinyl, benzoxazolyl, benzothiazolyl, benzimidazolyl, indolyl and the like.

As a further aspect of the present invention, there is provided a curable enamel composition further comprising one or more cross-linking catalysts, for example, dibutyl tin dilaurate; stearic acid; butyl stannoic acid; dibutyl tin oxide; zinc acetylacetonate; and 1,3-diacetoxy-1,1,3,3-tetrabutyldistannoxane.

As a further aspect of the present invention there is provided a cross-linkable enamel composition as described above, further comprising one or more leveling, rheology, and flow control agents such as silicones, fluorocarbons or cellulosics; flatting agents; pigment wetting and dispersing agents and surfactants; ultraviolet (UV) absorbers; UV light stabilizers; tinting pigments; defoaming and antifoaming agents; anti-settling, anti-sag and bodying agents; anti-skinning agents; anti-flooding and anti-floating agents; fungicides and mildewicides; corrosion inhibitors; thickening agents; or coalescing agents.

Specific examples of such additives can be found in *Raw Materials IndeX*, published by the National Paint & Coatings Association, 1500 Rhode Island Avenue, N.W., Washington, D.C. 20005.

Examples of flatting agents include synthetic silica, available from the Davison Chemical Division of W. R. Grace & Company under the tradename Syloid ®; polypropylene, available from Hercules Inc., under the tradename Hercoflat ®; synthetic silicate, available from J. M. Huber Corporation under the tradename Zeolex ®.

Examples of dispersing agents and surfactants include sodium bis(tridecyl) sulfosuccinnate, di(2-ethyl hexyl) sodium sulfosuccinnate, sodium dihexylsulfo-succinnate, sodium dicyclohexyl sulfosuccinnate, diamyl sodium sulfosuccinnate, sodium diisobutyl sulfo-succinnate, disodium iso-decyl sulfosuccinnate, disodium ethoxylated alcohol half ester of sulfosuccinnic acid, disodium alkyl amido polyethoxy sulfosuccinnate, tetrasodium N-(1,2-dicarboxy-ethyl)-N-oxtadecyl sulfo-succinnamate, disodium N-octasulfosuccinnamate, sulfated ethoxylated nonylphenol, 2-amino-2-methyl-1-propanol, and the like.

Examples of viscosity, suspension, and flow control agents include polyaminoamide phosphate, high molecular weight carboxylic acid salts of polyamine amides, and alkylene amine salts of an unsaturated fatty acid, all available from BYK Chemie U.S.A. under the tradename Anti Terra ®. Further examples include polysiloxane copolymers, polyacrylate solution, cellulose esters, hydroxyethyl cellulose, hydrophobically-modified hydroxyethyl cellulose, hydroxypropyl cellulose, polyamide wax, polyolefin wax, carboxymethyl cellulose, ammonium polyacrylate, sodium polyacrylate, and polyethylene oxide.

Several proprietary antifoaming agents are commercially available, for example, under the tradename Brubreak of Buckman Laboratories Inc., under the Byk ® tradename of BYK Chemie, U.S.A., under the Foamaster ® and Nopco ® tradenames of Henkel Corp./Coating Chemicals, under the Drewplus ® tradename of the Drew Industrial Division of Ashland Chemical Company, under the Troysol ® and Troykyd ® tradenames of Troy Chemical Corporation, and under the SAG ® tradename of Union Carbide Corporation.

Examples of fungicides, mildewicides, and biocides include 4,4-dimethyloxazolidine, 3,4,4-trimethyloxazolidine, modified barium metaborate, potassium N-hydroxy-methyl-N-methyldithiocarbamate, 2-(thiocyano-methylthio) benzothiazole, potassium dimethyl dithio-carbamate, adamantane, N-(trichloromethylthio) phthalimide, 2,4,5,6-tetrachloroisophthalonitrile, orthophenyl phenol, 2,4,5-trichlorophenol, dehydroacetic acid, copper naphthenate, copper octoate, organic arsenic, tributyl tin oxide, zinc naphthenate, and copper 8-quinolinate.

Examples of U.V. absorbers and U.V. light stabilizers include substituted benzophenone, substituted benzotriazoles, hindered amines, and hindered benzoates, available from American Cyanamide Company under the tradename Cyasorb UV, and diethyl-3-acetyl-4-hydroxy-benzyl-phosphonate, 4-dodecyloxy-2-hydroxy benzophenone, and resorcinol monobenzoate.

Such paint or coating additives as described above form a relatively minor proportion of the enamel composition, preferably about 0.05 weight % to about 5.00 weight %.

As a further aspect of the present invention, there is provided a curable enamel composition optionally containing one or more of the above-described additives.

As a further aspect of the present invention, there is provided the above enamel composition further comprising one or more other crosslinking agents. Typical crosslinking agents useful in this context include various melamine-type crosslinking agents, i.e., crosslinking agents having a plurality of N-CH$_2$OR groups with R=$C_1$-$C_8$ alkyl. In this regard preferred melamine-type crosslinking agents include hexamethoxy methylolmelamine, hexabutoxymethylolmelamine, and various hexaalkoxymethylol melamines in which the alkoxy group can be $C_1$-$C_8$ alkyl and mixtures thereof. Also included are tetramethoxymethylolbenzoguanamine, tetra-methoxymethylol urea and the corresponding hexaalkoxy-methylol derivatives.

Other crosslinkers which can be used in conjunction with the compounds of the invention include various aliphatic and aromatic polyisocyanates such as isophorone diisocyanate, tetramethyl xylylene diiso-cyanate, hexamethylene diisocyanate, methylene-bis-(4,4'-cyclohexylisocyanate), toluene diisocyanate, methylene-bis(4,4'-phenyl isocyanate) and the like. The above isocyanates can be used in either the blocked or unblocked forms and can be derivitized in a number of fashions. These derivitized isocyanates include isocyanurates, biurets, allophanates, and uritidine diones.

(See, for example, J. K. Backus in *High Polymers*, Vol. 29, 1977, p. 642–680).

As a further aspect of the present invention, there is provided a curable enamel composition as set forth above, further comprising one or more pigments in a concentration of about 1 to about 70 weight percent, preferably about 30 to about 60 weight percent, based on the total weight of components (a) and (b) of the composition.

Pigments suitable for use in the enamel compositions envisioned by the present invention are the typical organic and inorganic pigments, well-known to one of ordinary skill in the art of surface coatings, especially those set forth by the *Colour Index*, 3d Ed., 2d Rev., 1982, published by the Society of Dyers and Colourists in association with the American Association of Textile Chemists and Colorists. Examples include, but are not limited to the following: CI Pigment White 6 (titanium dioxide); CI Pigment Red 101 (red iron oxide); CI Pigment Yellow 42, CI Pigment Blue 15, 15:1, 15:2, 15:3, 15:4 (copper phthalocyanines); CI Pigment Red 49:1; and CI Pigment Red 57:1.

Upon formulation above, the curable enamel compositions is then applied to the desired substrate or article, e.g., steel, aluminum, or galvanized sheeting (either primed or unprimed), heated (i.e., cured) to a temperature of about 140° C. to about 275° C., for a time period of 1–120 minutes and subsequently allowed to cool. Thus, as a further aspect of the present invention, there is provided a shaped or formed article which has been coated with the thermosetting coating compositions of the present invention and cured.

Further examples of typical application and curing methods can be found in U.S. Pat. Nos. 4,737,551 and 4,698,391, incorporated herein by reference.

As a further aspect of the present invention, there is provided a coating which results from the application and curing of the curable enamel composition as set forth above.

EXPERIMENTAL SECTION $^1$H and $^{13}$C NMR spectra were obtained on a Varian Model Gemini 300 in CDCl$_3$ at frequencies of 300 and 75 MHz respectively. Carbon multiplicities, when given, were determined by the DEPT pulse sequence. (See, for example, Doddrell, D. M.; Pegg, D. T.; Bendall, M. R.; *J. Magn. Resort.* 48, 323, (1982).) Mass spectra were obtained on either a VG ZAB or 7070VSEQ. High resolution CI mass spectra (HR-CIMS) were obtained according to the method of Haddon et al., Proceedings of 36th ASMS Conf. June 5–8, (1988), 1396.

The applicable test procedures are as follows:
1. Testing Coated Metal Specimens at 100 Percent Relative Humidity Cleveland Humidity test (ASTM Method D 2247)
2. Ford Cup Viscosity (ASTM Method D 1200)
3. Film Thickness (General Electric Gage, Type B)
4. Film Hardness (Pencil Method, ASTM 3363-74, Reapproved 1980)
5. Solvent Resistance (methylethyl ketone (MEK) dynamic rub test, ASTM Method D 1308)
6. Impact Resistance (ASTM Method D 2794-84)
7. Resin molecular weight-GPC
8. OH Value determined by titration and are in units of mg KOH consumed per gram of polymer.
9. Acid Number (ASTM Method D 465). The units of this value are same as the OH value.

The following resins were used in the evaluations:

RESIN A: This material was an acrylic resin prepared from 20 mol % hydroxyethyl methacrylate and 80 mol % methyl methacrylate and had a hydroxyl value of 106. The resin was used as a 60% solids solution in ethyl 3-ethoxypropionate (EEP).

RESIN B: This material was a polyester prepared using a two-stage addition procedure from 16.1 moles neopentyl glycol, 5.0 moles trimethylolpropane, 11.8 moles cyclohexane dicarboxylic acid and 8.9 moles phthalic anhydride. The material had a Mw=16000, a Mn=2400 a hydroxyl value of 94 and an acid value of 9. This material was thinned with xylene and used as a 65–75% solids solution.

RESIN C: This material was prepared from 12.60 mol terephthalic acid, 0.66 mol 1,4-cyclohexandicarboxylic acid and 15.20 mol 1,6-hexane-diol. The resulting material had a hydroxyl number value of 42.5, an acid value of 2.3, a Mn of 3666 and a Mw of 9027.

RESIN D: This material was an amorphous polyester which contained terephthalic acid, neopentyl glycol and 9–10% (relative to neopentyl glycol) trimethylol propane. It had a hydroxyl number of 65, an acid value <10, a Mn of approximately 3000 and a Mw of ca. 10,000.

RESIN E: This material was prepared by two stage condensation of 3.12 mol NPG, 1.38 mol TMP, 1.47 mol dimethyl cyclohexanedicarboxylate and 2.21 mol isophthalic acid. The resulting resin had a OH value of 152 and an acid number of 2.1.

EXAMPLE 1

Preparation of 2,4-diacetyl-di-t-butyl-glutarate (1a)

In a 1 L, 3-neck flask equipped with mechanical stirrer, nitrogen inlet and thermometer was placed 500.04 g (3.161 mol) t-butyl acetoacetate (tBAA) and 158.16 g aqueous formaldehyde (30% formaldehyde, 1,582 mol). The flask was placed in an ice-water bath and 10.3 g Amberlite ® IRA 400 (OH) catalyst were added. The solution exothermed to ca. 35° C. upon addition of the catalyst. The reaction mixture was stirred at room temperature for 4 days, after which time the catalyst was recovered by filtration and the organic phase separated from the aqueous layer. The crude organic material was purified by wiped-film distillation at 130–140° C./0.2 mm Hg. An analytical sample was obtained by recrystallizing the distilled material from MeOH/H$_2$O and washing the resultant crystals with cold heptane, mp 46.5°–49.5° C.

$^1$H NMR (CDCl$_3$) 1.43 (s, 18 H), 2.18–2.23 (m, 2H), 2.20 (s, 6H), 3.38 (t, J=7.33 Hz, 2H). $^{13}$C NMR: 25.25 (CH$_2$), 27.58 (CH$_3$), 28.69 (CH$_3$), 57.62 (CH), 82.26 (C), 168.38 (C), 202.94 (C). IR: 2890–2860, 1730, 1710, 1150 cm$^{-1}$. Anal. Found C:62.30%, H:8.93% (Calcd. for C$_{17}$H$_{28}$O$_6$: C 62.16%, H 8.61 %). HR-CIMS 346.2213 (Calcd for C$_{17}$H$_{28}$O$_6$+NH$_4$: 346.2221).

EXAMPLE 2

Preparation of 2,4-diacetyl-di-(ethyl)-glutarate. (1c)

This material was prepared as above by stirring 500 g (3.84 mol) ethyl acetoacetate (EAA), 189 g of 37% aqueous formaldehyde (2.33 mol) and 10.3 g Amberlyst IR 400 (OH) for 3 days. The resulting homogenious solution was extracted with satd. NaCl/CH$_2$Cl$_2$, concentrated in vacuo and vacuum stripped on a wiped-film still at wall temperatures of 115° C./2 mm Hg. The crude oil was wiped-film distilled at 165° C./0.4 mm.

$^1$H NMR: 1.21 (t, J=7.14 Hz, 6H), 2.20 (s, 6H), 2.21-2.34 (m, 2H), 3.48 (t, J=7.15 Hz, 2H), 4.13 (q, J=7.15 Hz, 4H).

COMPARATIVE EXAMPLE 1

This example illustrates the utility of the basic ion exchange resin catalyst. In two identical round bottom flasks equipped with nitrogen inlet and magnetic stirrer was placed 46.96 g (0.361 mol) EAA and 12.96 g (0.159 mol) 37% aqueous formaldehyde. In one flask was placed 1.46 g Amberlite IR 400 (OH) catalyst while the other flask was left without catalyst. The reactions were monitored by gas chromatography. The course of the reaction versus time was as follows:

| Time | % EAA Remaining −1 (with catalyst) | −2 (no catalyst) |
| --- | --- | --- |
| initial | 80.3 | 100 |
| 1.5 h | 69.0 | 88.6 |
| 4.5 | 50.1 | 79.7 |
| 6.5 | — | 71.1 |
| 16 | 39 | — |
| 21.5 | — | 50.8 |

COMPARATIVE EXAMPLE 2

In a 500 mL, 3-neck flask with magnetic stirrer, thermometer and nitrogen inlet was placed 210 mL (214.4 g, 1.648 mol) EAA, 80 mL (83.52 g, 0.787 mol) benzaldehyde and 2.2 mL piperdine in 5.5 mL ethanol. The solution was allowed to stand at room temperature for 4 days, after which time the solid mass was filtered and recrystallized from petroleum ether/acetone to give 193.85 g (71%) adduct which was latter shown to be the cyclohexyl derivative 2d.(R=C$_2$H$_5$, R$^2$=H)

$^1$H NMR: 0.79 (t, J=7.7 Hz, 3H), 1.05 (t, J=7.7 Hz, 3H), 1.24 (s, 3H), 2.48 (dd, J=13.1, 2 Hz, 1H), 2.71 (d, J=13.9 Hz, 1H), 3.02 (d, J=13.1 Hz, 1H), 3.62-3.74 (m, 2H), 3.76-3.91 (m, 2H), 3.91-4.11 (m, 2H), 7.18-7.24 (m, 5H). $^{13}$C NMR: 13.33 (CH$_3$), 13.67 (CH$_3$), 28.44 (CH$_3$), 45.11 (CH), 52.60 (CH$_2$), 56.90 (CH), 60.96 (CH$_2$), 62.42 (CH$_2$), 73.01 (C), 127.94 (CH), 128.21 (CH), 128.80 (CH), 138.28 (C), 167.94 (C), 174.20 (C), 201.72 (C). IR: 3510, 3090, 2990, 2970, 1739, 1709, 1459, 1375, 1180 cm$^{-1}$. FDMS: 348.

COMPARATIVE EXAMPLE 3

In a 1 L 3 neck flask equipped with magnetic stirrer and nitrogen inlet was placed 253.3 g (1.601 mol) tBAA, 83.52 g (0.79 mol) benzaldehyde and 2.2 mL piperdine in 5.5 mL ethanol. The solutions was stirred for 4 days with an additional 1 mL piperdine in 1.5 mL ethanol being added each day. The resultant solid was filtered and recrystallized from acetone to give 16.5 g (5%) cyclohexyl adduct 2b (R=t-butyl, R$^2$=C$_6$H$_5$) and 81.65 g (42%) benzylidene acetoacetate. For 2b: $^1$H NMR:

1.08 (s, 9H), 1.23 (S, 9H), 1.35 (s, 3H), 2.45 (dd, J=14.3, 2.3 HZ, 1H), 2.67 (d, J=14.4 HZ, 1H), 2.93 (d, J=12.3 HZ, 1H), 3.50 (d, J=12.6 HZ, 1H), 3.89 (app. t, J=12.2 Hz, 2H), 7.21-7.34 (m, 5H).

EXAMPLE 3

Preparation of 2,4-diacetyl-3-phenyl-di(t-butyl)-glutarate (1b)

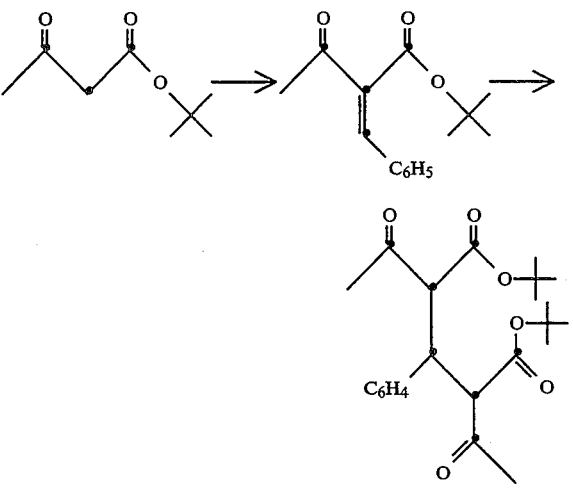

In a 3 L 3-neck flask equipped with nitrogen inlet, magnetic stirrer and thermometer was placed 442 g (4.166 mol) benzaldehyde, 671 g (4.242 mol) tBAA and 60 mL ethanol. The solution was cooled in an ice bath and 8.4 mL piperdine were added. The solution was stirred at 5°-25° C. for 18 h, after which time an additional 4 mL piperdine were added. After 24 h the crude solid was filtered and washed with acetone to give 570 g (56%) of a ca. 4:1 mixture of the E and Z t-butyl benzylidene acetoacetates as determined by integration of the acetoacetyl methyl peaks at 2.34 and 2.42 ppm.

(Michael Reaction of benzylidene acetoacetate with t-butyl acetoacetate). In an oven-dried 300 mL, 3-neck flask equipped with magnetic stirrer, nitrogen inlet, addition funnel and thermometer was placed 17.8 g (0.1125 mol) tBAA in 50 mL diethoxy methane (DEM). The solution was cooled to −14° C. and 1.21 g (0.0108 mol) potassium tert-butoxide were added. The solution was allowed to stir for 20 min and a solution of 25 g (0.1016 mol) t-butyl benzylidene acetoacetate in 75 mL DEM was added. After the addition was complete, the solution was stirred at −7°-0° C. for 3.5 h and subsequently extracted with satd. NH$_4$Cl. The organic phase was extracted with methylene chloride and washed with CuSO$_4$, water and brine. The resulting extract was dried over MgSO$_4$, concentrated in vacuo and recrystallized from acetone/petroleum ether to give 17.03 g (41%) 1b, (A=CHPh, R$^1$=CH$_3$, R=t-butyl) m.p. 133°-134° C. $^1$H NMR: 1.11 (s, 18H), 2.19 (s, 6H), 3.81 (d, J=9.8 Hz, 2H), 4.18 (t, J=9.8 Hz, 1H), 7.12-7.31 (m, 5H). $^{13}$C NMR: 27.34 (CH$_3$), 29.06 (CH$_3$), 43.10 (CH), 65.74 (CH), 82.08 (C), 127.28 (CH), 127.96 (CH), 129.78 (CH), 138.23 (C), 166.97 (C), 202.79 (C). IR (KBr): 3055, 2985, 2940, 1730, 1700, 1360, 1160 cm$^{-1}$. HR-FDMS: 404.2201 (Calcd. for C$_{23}$H$_{32}$O$_6$: 404.2190).

EXAMPLE 4

Preparation of 1,4-bis(2-acetopropane-carboxylic acid)benzene-di-t-butyl ester

In a 300 mL 3-neck flask equipped with nitrogen inlet, magnetic stirrer and thermometer was placed 20.9 g (0.156 mol) terephthalaldehyde, 49.73 g (0.314 mol)

tBAA and 110 mL methanol. When the solution became homogeneous 3 mL of a catalyst solution prepared from 2 mL piperdine, 0.3 mL acetic acid and 5 mL methanol was added. After 18 h the resultant solid mass was filtered, recrystallized from acetone/methanol and washed with heptane to give 38.9 g (60%) of product which was a mixture of the E,E; E,Z and Z,Z isomers.

$^1$H NMR: 1.527, 1.534 (s, 18H), 2.34, 2.41, 2.42 (s, 6H), 7.34–7.58 (m. 6 H). IR: 2995, 2975, 1720, 1660, 1620, 1391, 1365, 1245, 1155 cm.$^{-1}$ HR-FDMS 414.2046. (Calcd. for $C_{24}H_{30}O_6$: 414.2034). Anal. C 69.69%, H 7.62% (Calcd. for $C_{24}H_{30}O_6$: C 69.55% H 7.48%).

The resultant material was hydrogenated by placing 10.64 g (0.0257 tool) unsaturated bis (acetoacetate), 100 mL ethyl acetate and 0.2 g 5% Pd on carbon in a Fischer-Porter pressure bottle. The vessel was purged with nitrogen, and subsequently pressurized to a static pressure of 75 psi with hydrogen gas and maintained at that pressure for 13 h. The catalyst was removed by filtration and the resulting product purified by crystallization from acetone/heptane to give 8.96 g (83%) product, m.p. 89°–90.5° C.

$^1$H NMR: 1.39 (s, 18H), 2.17 (s, 6H), 3.06 (m, 4H), 3.65 (t, J=7.7 Hz, 2H), 7.09 (s, 4H). $^{13}$C NMR: 27.63 ($CH_3$), 29.23 ($CH_3$), 33.27 ($CH_2$), 62.19 (CH), 82.07 (C), 129.11 (CH), 136.80 (C), 168.55 (C), 203.23 (C). IR (KBr): 2965, 2919, 1731, 1711, 1649, 1631, 1365, 1144 cm$^{-1}$. MS (EI) 306 (11), 289 (10), 204 (20), 144 (95), 69 (45), 57 (100). HR-CIMS 436.2699 (Calcd for $C_{24}H_{34}O_6+NH_4$: 436.2699). Anal. C 68.75 %, H 8.44 % (Calcd for $C_{24}H_{34}O_6$: 68.88 %, H 8.19%).

EXAMPLES 5–8 AND COMPARATIVE EXAMPLE 5

Formulations were prepared from Compound 1a and Acrylic resin A as follows:

| Example No. | 5 | 6 | 7 | 8 | C-5 |
|---|---|---|---|---|---|
| 1a | 5.33 | 4.74 | 4.48 | 3.85 | — |
| Resin A (as 100% solids) | 15.66 | 15.35 | 16.07 | 16.54 | 15.00 |
| Solvent (mL) | 20 | 17 | 20 | 20 | 16.5 |

Solvent = 55:45 EEP/MAK

The formulations were drawn down on phosphated steel to various thicknesses and cured at 180°–190° C.. The properties of the resulting formulations are given in Table 1. The improved MEK rub resistance data for formulations 5–8 relative to C-5 indicate that material 1a is crosslinking acrylic polymer A.

EXAMPLE 9 AND COMPARATIVE EXAMPLES 6 AND 7

Formulations were prepared from Compounds 1a, the ethyl analogue of 1a and Polyester resin B as follows:

| Example No. | 9 | C-6 | C-7 |
|---|---|---|---|
| 1a (Example 1) | 8.32 | — | — |
| Resin B (as 100% solids) | 32.56 | 22.35 | 15.32 |
| Solvent (mL) | 6 | 4 | 6 |
| diethyl 2,4-diacetyl glutarate (Example 2) | | 4.75 | |

(Solvent = 80/20 MAK/EEP)

The formulations were drawn down and cured at 190°–240° C. as before. The results of these tests (Table 2) demonstrate that compound 1a is effective as a crosslinker for the polyester when compared to the control system containing no crosslinker or to the material of Example 2.

EXAMPLES 10–15 AND COMPARATIVE EXAMPLES 8–12

Use of common catalysts in coating formulations

Formulations were prepared as before from compound 1a and polyester B. The following catalysts were added to the formulations:

| Example No. | 10 | 11 | 12 | 13 | 14 | 15 |
|---|---|---|---|---|---|---|
| Compound 1a | 6.32 | 4.75 | 6.76 | 6.77 | 2.64 | 7.44 |
| Resin B as 100% solids | 29.99 | 18.75 | 31.67 | 31.86 | 12.50 | 34.91 |
| Solvent (mL) | 11 | 7 | 13 | 13 | 5 | 10 |
| Dibutyl tin dilaurate | 0.47 | — | — | — | — | — |
| Stearic Acid | — | 0.348 | — | — | — | — |
| Butyl stannoic Acid | — | — | 0.494 | — | — | — |
| Dibutyl tin oxide | — | — | — | 0.496 | — | — |
| Diacetyl tetrabutyl-di-stannoxane | — | — | — | — | 0.21 | — |
| zinc acetyl-acetonate | — | — | — | — | — | 0.544 |

(Solvent = 80/20 MAK/EEP)

| Comparative Example # | C-8 | C-9 | C-10 | C-11 | C-10 |
|---|---|---|---|---|---|
| Compound 1a | 3.53 | 5.55 | 4.1 | 3.40 | 3.40 |
| Resin B as 100% solids | 16.63 | 26.12 | 19.56 | 16.10 | 16.10 |
| Solvent (mL) | 7 | 10.5 | 7 | 6 | 6 |
| p-toluene sulfonic acid | 0.26 | | | | |
| Manganese acetate | | 0.41 | | | |
| Nickel Acetyl-acetonate | | | 0.30 | | |
| Zinc Acetate | | | | 0.25 | |
| Sodium Acetate | | | | | 0.25 |

The effect of the additives on the MEK resistance at various temperatures is given in Table 3. Examination of this data indicates that catalysts used in Examples 10–15 effectively lower the cure temperature while the materials used in Comparative Examples 8–10 either have no effect or a negative effect on the cure behavior of the compounds.

EXAMPLE 16 AND COMPARATIVE EXAMPLE 13

A formulation was prepared from Resin B and crosslinker 3a as follows:

| Example No. | 16 | C-13 |
|---|---|---|
| Crosslinker 3a (From Example 4) | 4.70 | — |
| Solvent (mL) | 7 | 7 |
| Resin B | 11.90 | 9.57 |

The formulations were evaluated as before, the results of these evaluations are summarized in Table 4. The MEK resistance properties and impact strength of the resultant coatings indicates that material 3a is also an effective crosslinker.

EXAMPLES 17–19

Use of di-t-butyl-3,5-diacetyl-4-phenyl glutarate as a crosslinker for polyesters The following formulations were prepared:

| Example No. | 17 | 18 | 19 |
|---|---|---|---|
| Compound 1b (from Example 3) | 0.154 | 0.346 | 2.578 |
| Polyester C | 0.842 | | |
| Polyester D | | 1.648 | |
| Polyester E | | | 6.72 |
| Solvent | 3.0 g | 2.25 g | |

The formulations were heated in vials at 180°–220° C. Insoluble gels, indicative of crosslinked polymers, resulted.

EXAMPLE 20 AND COMPARATIVE EXAMPLE 14

This example illustrates the improved humidity resistance obtained in coating formulations employing compound 1a.

Pigmented formulations were prepared according to the following formulations:

| Example No. | 20 | C-14 |
|---|---|---|
| Compound 1a | 4.78 | — |
| Resin B (100% solids) | 11.16 | 11.16 |
| TiO$_2$ | 10.63 | 7.44 |

The panels were drawn down and cured at 230° C. as before. The formulations of Example 20 showed no blistering after >1000 hrs of exposure to Cleveland Humidity conditions, while formulation C-14 showed considerable blistering after 727 h exposure.

EXAMPLE 21

Formulations were prepared from compound 1b and Resin A as follows:

| Example No. | 21 |
|---|---|
| Compound 1b | 5.52 |
| Resin A (100% solids) | 14.48 |
| Solvent (mL) | 10 |

Solvent (70/15/15 MAK:EEP:nBuOH)

TABLE 1

| Example No. | Cure[a] Conditions | Thickness (mils) | Impact[b] (F/R) | Pencil Hardness | MEK RUB |
|---|---|---|---|---|---|
| 5 | 180/30 | 0.45 | 140/40 | 7H | 415 |
| 5 | 180/30 | 1.03 | 160/20 | 7H | 350 |
| 5 | 190/30 | 1.10 | 60/0 | 7H | 560 |
| 6 | 180/30 | 0.47 | 140/60 | 7H | 400 |
| 6 | 180/30 | 1.12 | 160/0 | 7H | 304 |
| 6 | 190/30 | 1.00 | 60/0 | 7H | >600 |
| 7 | 180/30 | 0.55 | 160/80 | 7H | 400 |
| 7 | 180/30 | 1.07 | 160/0 | 7H | 437 |
| 7 | 190/30 | 1.00 | 80/0 | 7H | >600 |
| 8 | 180/30 | 0.59 | 160/100 | 7H | 350 |
| 8 | 180/30 | 1.09 | 160/0 | 7H | 500 |
| 8 | 190/30 | 0.99 | 60/0 | 7H | 550 |
| C-5 | 180/30 | 0.65 | 80/0 | 5H | <150 |
| C-5 | 180/30 | 1.18 | 0/0 | 5H | <150 |
| C-5 | 190/30 | 1.14 | 60/0 | 5H | <120 |

[a]Temperature (°C.) and time (min) respectively.
[b]Forward and reverse impact strength, respectively, in foot lbs.

TABLE 2

| Example No. | Cure[a] Conditions | Thickness (mils) | Impact[b] (F/R) | Pencil Hardness | MEK RUB |
|---|---|---|---|---|---|
| 9 | 210/30 | 0.65 | 160/40 | 2H | 60 |
| 9 | 220/30 | 0.86 | 160/60 | 3H | 412 |
| 9 | 230/30 | 0.56 | 160/160 | 2H | 205 |
| C-6 | 210/30 | 0.84 | 160/40 | H | 110 |
| C-6 | 220/30 | 0.88 | 160/40 | H | 103 |
| C-6 | 230/30 | 0.78 | 160/120 | 4H | 75 |
| C-7 | 210/30 | 0.80 | 160/40 | 2H | 55 |
| C-7 | 220/30 | 1.02 | 160/40 | H | 139 |
| C-7 | 230/30 | 0.78 | 160/140 | 2H | 79 |

[a]Temperature (°C.) and time (min) respectively.
[b]Forward and Reverse impact strength, respectively, in foot lbs.

TABLE 3

| Ex. No. | Cure Conditions | Thickness (mils) | Impact[b] (F/R) | Pencil Hardness | MEK RUB | Comments |
|---|---|---|---|---|---|---|
| 10 | 210/30 | 0.99 | 160/0 | F/H | 100 | |
| 10 | 220/30 | 0.94 | 160/160 | 2H/3H | 500 | |
| 11 | 210/30 | 0.75 | 160/40 | 2H/3H | 57 | |
| 11 | 220/30 | 0.70 | 160/160 | 2H/3H | 285 | |
| 12 | 210/30 | 0.96 | 160/120 | H/2H | >500 | |
| 12 | 220/30 | 1.11 | 160/160 | 2H/3H | >500 | |
| 13 | 210/30 | 0.76 | 160/20 | F/H | 243 | |
| 13 | 220/30 | 0.75 | 160/160 | H/2H | 77 | |
| 14 | 210/30 | 0.95 | 160/80 | | 301 | |
| 14 | 220/30 | 0.99 | 160/160 | | 250 | |
| 15 | 210/30 | 1.34 | 160/0 | B/HB | 194 | |
| 15 | 220/30 | 1.22 | 160/0 | H/2H | 370 | |
| C-8 | | Coating bubbled and was highly colored. | | | | Properties could not be determined. |
| C-9 | 210/30 | 0.57 | 160/20 | 2H/5H | 51 | Dark and discolored |
| C-9 | 220/30 | 0.51 | 160/80 | 5H/6H | 30 | Very dark |
| C-10 | 210/30 | 0.89 | 140/0 | B/HB | 15 | Dark and discolored |
| C-10 | 220/30 | 0.90 | 160/0 | B/HB | 95 | Dark and dis- |

TABLE 3-continued

| Ex. No. | Cure Conditions | Thickness (mils) | Impact[b] (F/R) | Pencil Hardness | MEK RUB | Comments |
|---|---|---|---|---|---|---|
| C-11 | 210/30 | 0.99 | 140/0 | | <10 | colored Slightly discolored |
| C-11 | 220/30 | 1.01 | 160/0 | | 40 | Discolored |
| C-12 | 210/30 | 1.07 | 140/0 | | <10 | Dark and discolored |
| C-12 | 220/30 | 0.81 | 160/0 | | 15 | Dark and discolored |

[a]Temperature (°C.) and time (min) respectively.
[b]Forward and reverse impact strength, respectively, in foot. lbs.

TABLE 4

| Example No. | Cure[a] Conditions | Thickness (mils) | Impact[b] (F/R) | Pencil Hardness | MEK RUB |
|---|---|---|---|---|---|
| 16 | 190/30 | 0.70 | 160/0 | B/HB | 20 |
| 16 | 200/30 | 0.61 | 160/20 | H/2H | 185 |
| 16 | 205/30 | 0.80 | 160/100 | H/2H | 175 |
| 16 | 210/30 | 0.66 | 160/20 | H/2H | 40 |
| C-13 | 190/30 | 0.80 | 160/0 | 3B/2B | <10 |
| C-13 | 200/30 | 0.85 | 160/120 | B/HB | <10 |
| C-13 | 205/30 | 0.64 | 160/100 | H/2H | 30 |
| C-13 | 210/30 | 0.78 | 160/0 | H/HB | <10 |

[a]Temperature (°C.) and time (min) respectively.
[b]Forward and reverse impact strength, respectively, in foot lbs.

We claim:

1. A process for preparing a compound of the formula

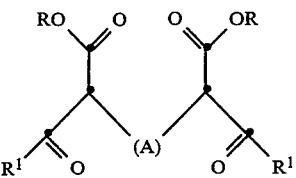

wherein A is a group of the formula —CH$_2$—, R is C$_4$-C$_{10}$ tertiary alkyl, and R$^1$ is C$_1$-C$_6$ alkyl or aryl, which comprises contacting a mixture comprised of a compound of the formula

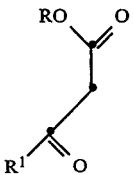

and aqueous formaldehyde with a basic ion exchange resin.

2. The process of claim 1, wherein R is t-butyl.
3. The process of claim 1, wherein R$^1$ is methyl.
4. The process of claim 1, wherein R$^1$ is phenyl.

* * * * *